United States Patent [19]
Kunz

[11] Patent Number: 5,126,358
[45] Date of Patent: Jun. 30, 1992

[54] PLANT-PROTECTIVE COMPOSITIONS

[75] Inventor: Walter Kunz, Oberwil, Switzerland

[73] Assignee: Ciba-Geigy Corporation, Ardsley, N.Y.

[21] Appl. No.: 632,771

[22] Filed: Dec. 21, 1990

Related U.S. Application Data

[60] Division of Ser. No. 403,844, Sep. 1, 1989, Pat. No. 5,015,649, which is a continuation of Ser. No. 187,161, Apr. 28, 1988, abandoned.

[30] Foreign Application Priority Data

Apr. 29, 1987 [CH] Switzerland ............... 1629/87

[51] Int. Cl.$^5$ ............... A61K 31/44; C07D 401/12
[52] U.S. Cl. ............... 514/333; 514/335; 546/261; 546/256; 546/262; 546/263; 546/265
[58] Field of Search ............... 546/256; 514/333

[56] References Cited

U.S. PATENT DOCUMENTS

| | | | |
|---|---|---|---|
| 3,962,260 | 6/1976 | Ruetman | 546/294 |
| 4,137,067 | 1/1979 | Gätzi | 71/94 |
| 4,966,908 | 10/1990 | Eckhardt et al. | 514/340 |
| 4,980,355 | 12/1990 | Zondler et al. | 514/256 |

FOREIGN PATENT DOCUMENTS

| | | |
|---|---|---|
| 0253468 | 1/1988 | European Pat. Off. |
| 0711756 | 7/1954 | United Kingdom |

OTHER PUBLICATIONS

Chem. Abstr. 86:106533s (1977).
Chem. Abstr. 57:4769a (1962).

*Primary Examiner*—Jane T. Fan
*Attorney, Agent, or Firm*—Marla J. Mathias; Edward McC. Roberts

[57] ABSTRACT

The invention relates to novel isonicotinoylpyridinyl hydrazine derivatives of formula I

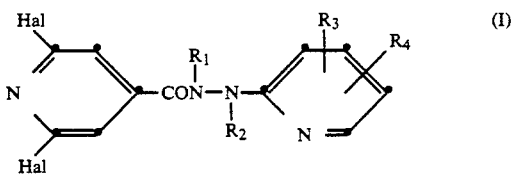

wherein
Hal is halogen,
$R_1$ is hydrogen, methyl or —$COR_5$,
$R_2$ is hydrogen, $C_1$–$C_4$alkyl, or a radical selected from —$COR_5$ and —CO—Z—$R_6$,
$R_3$ is hydrogen, halogen, trifluoromethyl, trichloromethyl, —COOH, —$COOCH_3$, —OH or nitro.
$R_4$ is hydrogen, halogen, methoxy or methyl,
$R_5$, $R_6$, Z are as defined hereinafter.
with the exception of 1-(pyridin-2'-yl)-2-(2,6-dichloroisonicotinoyl) hydrazine.

The novel compounds have plant-protective properties and are especially suitable for protecting plants from attack by phytopathogenic microorganisms such as fungi, bacteria and viruses.

19 Claims, No Drawings

PLANT-PROTECTIVE COMPOSITIONS

This is a divisional of Ser. No. 403,844, filed on Sep. 1, 1989, which is a continuation of Ser. No. 187,161, filed on Apr. 28, 1988, now abandoned, now U.S. Pat. No. 5,015,649 issued May 14, 1991.

The present invention relates to novel substituted isonicotinoylpyridinyl hydrazine derivatives of formula I below. The invention also relates to the preparation of these compounds and to compositions which contain at least one of said novel compounds as active component. The invention also relates to the preparation of the novel compositions and to the use of the compounds of this invention, or the compositions containing them, for protecting plants against attack by harmful microorganisms, for example phytopathogenic fungi, bacteria and viruses.

The compounds of this invention have the formula I

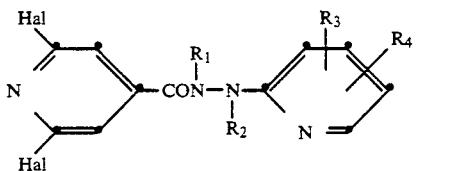
(I)

wherein
Hal is halogen,
$R_1$ is hydrogen, methyl or $-COR_5$,
$R_2$ is hydrogen, $C_1-C_4$alkyl, or a radical selected from $-COR_5$ and $-CO-Z-R_6$,
$R_3$ is hydrogen, halogen, trifluoromethyl, trichloromethyl, $-COOH$, $-COOCH_3$, $-OH$ or nitro,
$R_4$ is hydrogen, halogen, methoxy or methyl,
$R_5$ is $C_1-C_6$alkyl, unsubstituted or substituted by one or more halogen atoms, $C_1-C_6$alkyl which is interrupted by oxygen or sulfur, $C_1-C_6$-alkyl which is substituted by one or more halogen atoms and interrupted by oxygen or sulfur; $C_2-C_4$alkenyl, unsubstituted or substituted by one or more halogen atoms; phenyl, benzyl, or phenyl or benzyl each substituted by halogen, methyl, trifluoromethyl or trichloromethyl; a 5- or 6-membered heterocycle which contains nitrogen, oxygen or sulfur as hetero atoms, a 3- to 6-membered cycloalkyl radical or a cycloalkyl radical which is substituted by one or more halogen atoms or methyl groups,
$R_6$ is $C_1-C_5$alkyl, phenyl or, if Z is the $-CO$ group, is O-alkyl containing 1 or 2 carbon atoms, and
Z is oxygen, sulfur or the $-CO$ group,
with the exception of 1-(pyridin-2'-yl)-2-(2,6-dichloroisonicotinoyl) hydrazine.

Halogen by itself or as moiety of another substituent is fluorine, chlorine, bromine or iodine, with fluorine, chlorine or bromine being preferred.

Alkyl by itself or as moiety of another substituent denotes straight chain or branched alkyl groups. Depending on the indicated number of carbon atoms, alkyl is typically: methyl, ethyl as well as the isomers of propyl, butyl, pentyl or hexyl, for example isopropyl, isobutyl, tert-butyl, sec-butyl or isopentyl.

Alkenyl may be, for example, 1-propenyl, allyl, 1-butenyl, 2-butenyl or 3-butenyl.

Cycloalkyl may be cyclopropyl, cyclobutyl, cyclopentyl or cyclohexyl, and is preferably cyclopropyl, cyclopentyl or cyclohexyl. The preferred substituted cycloalkyl radical is 2,2-dimethyl-3,3-dichlorocyclopropyl.

Examples of preferred 5- or 6-membered heterocycles containing nitrogen, oxygen and/or sulfur as hetero atoms are: thiophene, thiazole, furan, pyridine, thiadiazole, including 1,2,3-thiadiazole.

On account of their pronounced plant-protective microbicidal properties, those compounds of formula I are preferred which contain the following substituents or combinations thereof:

1) Hal is chlorine or bromine;
$R_1$ is hydrogen;
$R_2$ is hydrogen, methyl, ethyl or a group selected from $-COCH_3$, $-COC_2H_5$ or

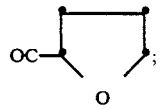

and
$R_3$ and $R_4$ are each independently of the other hydrogen, halogen or trifluoromethyl.

2) Hal is chlorine;
$R_1$ is hydrogen;
$R_2$ is hydrogen, methyl or ethyl; and
$R_3$ and $R_4$ are each independently of the other hydrogen, halogen or trifluoromethyl.

3) Hal is chlorine;
$R_1$ is hydrogen;
$R_2$ is a group selected from $-COCH_3-$, $-COC_2H_5$ and

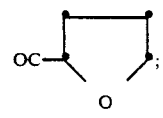

and
$R_3$ and $R_4$ are each independently of the other hydrogen, halogen or trifluoromethyl.

4) Hal is chlorine;
$R_1$ is hydrogen;
$R_2$ is hydrogen, methyl or ethyl; and
$R_3$ is hydrogen or 3-chloro; and
$R_4$ is hydrogen or 5-trifluoromethyl.

5) Hal is chlorine;
$R_1$ is hydrogen;
$R_2$ is a group selected from $-COCH_3-$, $-COC_2H_5$ or

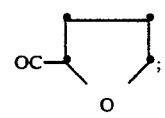

and
$R_3$ is hydrogen or 3-chloro; and
$R_4$ is hydrogen or 5-trifluoromethyl.

On account of their outstanding biological activity, the following compounds are preferred:
1-acetyl-1-pyridin-2'-yl)-2-(2,6-dichloroisonicotinoyl)-hydrazine;

1-propionyl-1-pyridin-2'-yl)-2-(2,6-dichloroisonicotinoyl)-hydrazine;

1-tetrahydrofuroyl-1-pyridin-2'-yl)-2-(2,6-dichloroisonicotinoyl)hydrazine;

1-(3'-chloro-5'-trifluoromethylpyridin-2'-yl)-(2,6-dichlorisonicotinoyl)hydrazine;

1-methyl-1-(3'-chloro-5'-trifluoromethylpyridin-2'-yl)-(2,6-dichlorisonicotinoyl)hydrazine;

1-ethyl-1-(3'-chloro-5'-trifluoromethylpyridin-2'-yl)-(2,6-dichloroisonicotinoyl)hydrazine.

The compound 1-(pyridin-2'-yl)-2-(2,6-dichloroisonicotinoyl) hydrazine has already been disclosed. So far, however, nothing is known about its biological properties. Surprisingly, this compound has now proved to be very active against plant diseases. As active component of compositions for protecting plants against diseases this compound constitutes an object of the present invention, as does also the use of said compound for this purpose.

The compounds of formula I are prepared by either
a) reacting 2-hydrazinopyridine derivatives of formula II

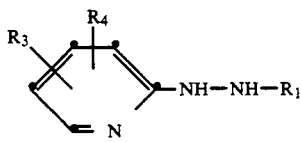

with 2,6-dihaloisonicotinoyl derivatives of formula III

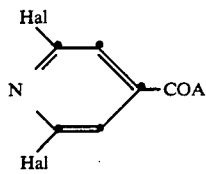

in an inert solvent, or b) reacting 2,6-dihaloisonicotinoyl hydrazide derivatives of formula IV

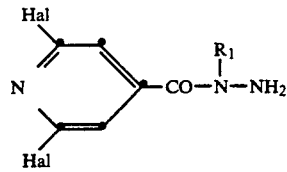

with substituted 2-halopyridine derivatives of formula V

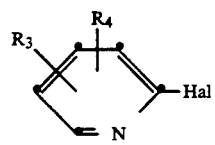

in an inert solvent and with or without a catalyst, and subsequently c) reacting the resultant compounds of formula Ia

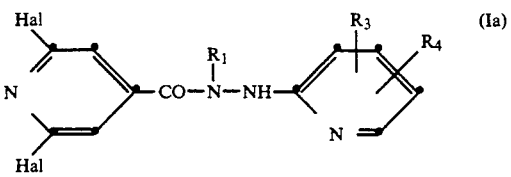

with compounds of formula VI $$R_2CO-Y \qquad (VI)$$

in an inert solvent and in the absence or presence of a base, in which formulae (II) to (VI) above A is halogen, O-alkyl of 1 to 4 carbon atoms or S-alkyl of 1 to 4 carbon atoms, Y is halogen or O-alkyl of 1 to 4 carbon atoms, and Hal and $R_1$ to $R_4$ are as defined for formula I.

The reaction temperatures of the individual process steps are, for (a) and (c), up to 180° C., preferably from 20° to 80° C., and, for (b), from −10° to +180° C., preferably from 0° to 70° C.

The use of an acid acceptor is advantageous in process step (c). Suitable acid acceptors are organic and inorganic bases, for example tertiary amines such as trialkylamines (trimethylamine, triethylamine, tripropylamine and the like), pyridine and pyridine bases (4-dimethylaminopyridine, 4-pyrrolidylaminepyridine and the like), alcoholates such as potassium tert-butylate, oxides, hydroxides, carbonates and bicarbonates of alkali metals and alkaline earth metals, as well as alkali metal acetates.

It can be advantageous to use a catalyst in the reaction of process step (b). Examples of suitable catalysts are: copper salts, preferably copper(I) chloride or copper(II) chloride or copper(I) acetate or copper(II) acetate.

Contingent on the respective reaction conditions, suitable inert solvents and diluents are used as reaction media for process steps (a) to (c). Examples of suitable solvents and diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxane, tetrahydrofuran; nitriles such as acetonitrile and propionitrile; N,N-dialkylated amides such as dimethylformamide; dimethylsulfoxide; ketones such as acetone, diethyl ketone, methyl ethyl ketone; and mixtures of the above solvents.

The starting materials can be prepared as follows:

The 2-hydrazinopyridines of formula II are prepared by reacting suitably substituted 2-halopyridines with hydrazine or methyl hydrazine. It is preferred to use 2-chloropyridines or 2-bromopyridines in this reaction. The reaction is normally conducted in a mixture of methanol/water and can be usefully speeded up by catalysis with mono- or divalent heavy metal ions such as copper(I) or copper(II) salts (q.v. Eur. J. Med. Chem. 10 (1975), 252; J. Org. Chem. 31, 260).

Compounds of formula II are obtained from 2,6-dihydroxyisonicotinic acid by treatment with phosphoroxy halide and, if appropriate, by esterification with the corresponding alcohol. The reaction with phosphoroxy halide takes place in the temperature range from 50° to 200° C. and under a pressure of 1 to 100·10⁵ Pa, and in the absence or presence of a base.

The isonicotinoyl hydrazides of formula IV are prepared, for example, by reacting alkyl esters of 2,6-dihaloisonicotonic acid with hydrazine or methyl hydrazine in the temperature range from 50° to 100° C. under normal pressure (and by further methods, q.v. U.S. Pat. No. 4,137,067; and also Eur. J. Med. Chem.—Chemica Therap. 10 (1975), 252).

Further methods of preparing the precursors, including also those of the substituted 2-halopyridine derivatives, are known to the skilled person or described in the literature.

Pyridinyl hydrazine derivatives have already been disclosed as compounds for use in different fields, for example as fungicides and bactericides in U.S. Pat. No. 3,962,260, and as tuberculostatic agents in Acta Fac. Pharm. Brun. Bratislav. 4, 65–95 (1962) [Chem. Abstr. Vol. 57 (1962) 4769a], as well as microbicides in U.S. Pat. No. 4,137,067.

Surprisingly, it has now been found that the novel compounds of formula I have a very useful activity spectrum for protecting plants against diseases caused by fungi as well as by bacteria and viruses. The mode of action of the compounds of this invention is directed in particular to generally increasing the power of resistance of the treated plants so as to achieve a broad antimicrobial resistance to a wide spectrum of harmful microorganisms. The great advantage of the novel compounds resides in the feature that, when they are applied for the treatment of plants, instead of direct action being exerted on the phytopathogenic microorganisms the plants' own biological defence mechanism is activated and stimulated, to that it is possible to ensure preservation of the health of the treated plants by their own efforts without any further direct application of microbicides during the vegetation period. Accordingly, the compounds of formula I are characterised in that they exert no direct action on microorganisms, but instead immunise healthy plants against plant diseases. This immunity to plant diseases arising therefrom can be utilised for protecting numerous cultivated plants, so that the occurrence of harmful microorganisms is effectively prevented on plants or parts of plants (fruit, blossoms, foliage, stalks, tubers, roots) in different crops of useful plants, while the parts of plants that grow later are also protected from phytopathogenic microorganisms. In contradistinction thereto, however, a number of compounds of formula I can also be used protectively against phytopathogenic microorganisms. The compounds of formula I act by means of foliar application as well as systemically. They can also be used as dressing agents for protecting seeds (fruit, tubers, grains) and plant cuttings against fungus infections, for example against Fusarium nivale, Helminthosporium gramineum, Ustilago nuda, as well as against phytopathogenic microorganisms which occur in the soil.

The activity spectrum of the compounds of formula I extends, for example, to phytopathogenic fungi belonging to the following classes: Fungi imperfecti (e.g. Botrytis, Pyricularia, Colletotrichum, Helminthosporium, Fusarium, Septoria, Cercospora and Alternaria); Basidiomycetes (e.g. the genera Hemileia, Rhizocotonia, Puccinia); Ascomycetes (e.g. Venturia, Podosphaera, Erysiphe Monilinia, Uncinula) and Phycomycetes (e.g. Phytophthora, Plasmopara). In addition, the compounds of this invention act against phytopathogenic bacteria and viruses (e.g. against Xanthomonas spp., Pseudomonas spp., *Erwinia amylovora*, and against the tobacco mosaic virus.

The invention also relates to the compositions which contain the compounds of formula I as active component, in particular to plant-protective compositions, and to the use thereof in agriculture or related fields.

The invention further embraces the preparation of these compositions, which comprises homogenously mixing the active component with one or more compounds or groups of compounds described herein. The invention furthermore relates to a method of treating plants, which comprises applying thereto the novel compounds of formula I or the novel compositions containing them.

Target crops to be protected within the scope of the present invention comprise e.g. the following species of plants: cereals (wheat, barley, rye, oats, rice, maize, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute) citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as tobacco, nuts, coffee, sugar cane, tea, pepper, vines, hops, bananas and natural rubber plants, as well as ornamentals (composites). This recitation constitutes no limitation.

The compounds of formula I are normally applied in the form of compositions and can be applied to the crop area or plant to be treated, simultaneously or in succession, with further compounds. These further compounds can be fertilisers, micronutrient donors or other substances that influence plant growth. It is also possible to use selective herbicides, insecticides, fungicides, bactericides, nematicides, molluscicides or mixtures of several of these substances, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the respective pathogen. However, the compound of formula I can also penetrate the plant through the roots via the soil (systemic action) by impregnating the locus of the plant with a liquid formulation, or by applying the compounds in solid form to the soil, e.g. in granular form (soil application). The compounds of formula I may also be applied to seeds (coating) by impregnating the seeds either with a liquid formulation containing a compound of formula I, or coating them with a solid formulation. In special cases, further types of application are also possible, e.g. selective treatment of the plant stems or buds, as well as the treatment of rice plants by into water application.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil, sunflower oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, which can be obtained e.g. from soya beans.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamino-propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, caster oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. stearyltrimethylammonium chloride or benzyl bis(2-chloroethyl)ethylammonium bromide.

Further surfactants customarily employed in formulation technology are known to the skilled person or can be found in the relevant literature.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Agrochemical compositions which contain the compounds of formula I as active component constitute an object of the present invention.

The invention is illustrated in more detail by the following non-limitative Examples.

1. PREPARATORY EXAMPLES

EXAMPLE 1.1: Preparation of

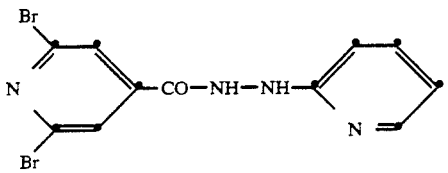

1-(Pyridin-2'-yl)-2-(2,6-dibromoisonicotinoyl) hydrazine 6.2 g of 23-hydraxinopyridine are dissolved in 50 ml of absolute pyridine and a solution of 17.6 g of 2,6-dibromoisonicotinoyl chloride in 10 ml of absolute acetonitrile is added dropwise, with stirring, while keeping the reaction temperature below 35° C. by cooling. After the reaction has subsided, the reaction mixture is heated and kept for 7 hours at 65° C., then cooled and poured into ca. 100 ml of ice-water. The precipitate is isolated by filtration and washed with water and an 8:2 mixture of hexane/diethyl ether and dried under vacuum, affording 17.4 g of white crystals with a melting point of 187°-190° C.

EXAMPLE 1.2: Preparation of

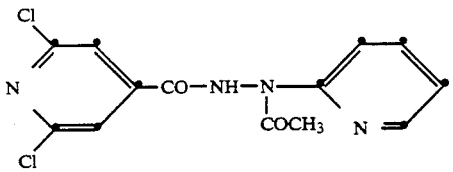

1-(Acetyl-1-pyridin-2'-yl)-2-(2,6-dichloroisonicotinoyl) hydrazine 4.2 g of the compound of Example 1.1 are added, in portions, to 20 ml of acetic anhydride and the resultant yellow suspension is heated for 2 hours to 85° C., whereupon a solution is obtained. Excess acetic anhydride is rapidly distilled off under vacuum and the residue is crystallised by the addition of a small amount of diethyl ether/petroleum ether. The precipitate is filtered with suction and washed with petroleum ether, affording 4.2 g of the title compound with a melting point of 128°-130° C.

EXAMPLE 1.3: Preparation of

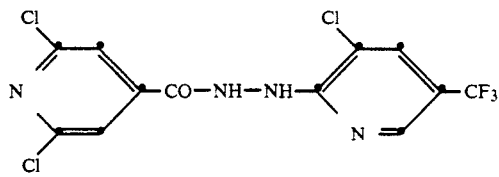

1-(3-Chloro-5-trifluoromethylpyridin-2'-yl)-2-(2,6-dichloroisonicotinoyl) hydrazine 50.2 g of 2,6-dichloroisonicotinoyl hydrazide are suspended in 250 ml of tetrahydrofuran and to the suspension are added 14 g of finely pulverised potassium hydroxide. Then 0.8 g of copper(II) acetate is added at 0°-5° C. and a solution of 57.5 g of 2,3-dichloro-5-trifluoromethylpyridine in 150 ml of tetrahydrofuran is added dropwise over ¾ hour. The cooling bath is then removed and the reaction mixture is refluxed overnight. A further 0.8 g of copper(II) acetate and 6 g of 2,3-dichloro-5-trifluoromethylpyridine are subsequently added and the reaction mixture is refluxed for another 24 hours. The reaction mixture is then concentrated to half its volume under vacuum and the residue is poured into ice-water and extracted with dichloromethane. The organic extract is washed with water and concentrated and purified through a column of silica gel (eluant: 1:1 mixture of ethyl acetate/diethyl ether), to give the title compound in the form of beige crystals with a melting point of 154°-155° C.

EXAMPLE 1.4: Preparation of

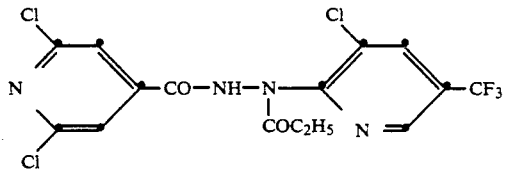

1-Propionyl-1-(3-chloro-5-trifluoromethylpyridin-2'-yl)-2-(2,6-dichloroisonicotinoyl) hydrazine 5.8 g of 2-(2,6-dichloroisonicotinoyl)-1-(3-chloro-5-trifluoromethylpyridin-2'-yl) hydrazine in 45 ml of tetrahydrofuran are added 16.5 ml of 1N sodium hydroxide solution and, with stirring, a solution of 1.5 ml of propionyl chloride in 4.5 ml of tetrahydrofuran is added dropwise at room temperature. The reaction mixture is stirred overnight at room temperature and then 25% of each of the indicated amounts of 1N sodium hydroxide solution and propionyl chloride are added. After a total reaction time of 48 hours, the reaction mixture is diluted with water, extracted with ethyl acetate, and the extracts are washed with water, dried, and concentrated by evaporation. The crystalline residue (6.5 g≙90% of theory) is suspended in a small amount of diethyl ether and isolated by filtration. The pure product has a melting point of 168°-170° C.

The following compounds are obtained in accordance with the above described procedures:

TABLE 1

Compounds of formula

| Compound | $X_1$ | $X_2$ | $R_1$ | $R_2$ | $R_3$ | $R_4$ | physical data |
|---|---|---|---|---|---|---|---|
| 1.1 | Cl | Cl | H | COCH$_3$ | H | H | m.p. 128–130° C. |
| 1.2 | Cl | Cl | CH$_3$ | COCH$_3$ | H | H | |
| 1.3 | Cl | Cl | H | COCH$_2$CH$_3$ | H | H | m.p. 137–139° C. |
| 1.4 | Cl | Cl | H | COCH$_3$ | 3-Cl | 5-CF$_3$ | m.p. 177–179° C. |
| 1.5 | Cl | Cl | H | COCH$_2$OCH$_3$ | H | H | m.p. 48–51° C. |
| 1.6 | Cl | Cl | H | COC(CH$_3$)$_3$ | H | H | m.p. 182–185° C. |
| 1.7 | Cl | Cl | H | COCH$_2$—C$_6$H$_5$ | H | H | m.p. 189–190° C. |
| 1.8 | Cl | Cl | H | CO-(2-furyl) | H | H | m.p. 164–166° C. |
| 1.9 | Cl | Cl | H | CO—CH$_2$—C$_6$H$_4$—Br | H | H | m.p. 170–172° C. |
| 1.10 | Cl | Cl | H | CO-(furyl) | H | H | m.p. 163–165° C. |
| 1.11 | Br | Br | H | COCH$_3$ | H | H | m.p. 157–160° C. |
| 1.12 | Cl | Cl | H | CO—CH$_2$—C$_6$H$_4$—CH$_3$ | 3-Cl | 5-CF$_3$ | m.p. 174–177° C. |
| 1.13 | Cl | Cl | H | COCH=CH—CH$_3$ | 3-Cl | 5-CF$_3$ | m.p. 173–176° C. |
| 1.14 | Cl | Cl | H | CO—C$_6$H$_{13}$-n | H | H | m.p. 105–107° C. |
| 1.15 | Cl | Cl | H | COCH$_2$CH$_3$ | 3-Cl | 5-CF$_3$ | $n_D^{50}$ = 1.5330 |
| 1.16 | Cl | Cl | H | CO-(3,5-dibromothienyl) | H | H | m.p. 204–207° C. |
| 1.17 | Cl | Cl | H | CO-(2,2-dimethyl-3,3-dichlorocyclopropyl) | H | H | |
| 1.18 | Br | Br | H | CO-(2,2-dimethyl-3,3-dichlorocyclopropyl) | 3-Cl | 5-CF$_3$ | |
| 1.19 | Cl | Cl | H | COCH$_3$ | 4-CF$_3$ | 6-Cl | |
| 1.20 | Cl | Cl | H | COCH$_3$ | 4-CCl$_3$ | 6-Cl | |
| 1.21 | Cl | Cl | H | COCH$_3$ | 4-CCl$_3$ | 6-OCH$_3$ | |
| 1.22 | Cl | Cl | H | COC$_2$H$_5$ | 4-COOCH$_3$ | 6-Cl | |
| 1.23 | Cl | Cl | H | COCH$_2$OCH$_3$ | 4-COOCH$_3$ | 6-Br | |

TABLE 1-continued

Compounds of formula

| Compound | $X_1$ | $X_2$ | $R_1$ | $R_2$ | $R_3$ | $R_4$ | physical data |
|---|---|---|---|---|---|---|---|
| 1.24 | I | I | H | ![CO-cyclopropane with (CH3)2 and Cl,Cl] | H | H | |
| 1.25 | Cl | Cl | H | COOCH$_3$ | H | H | |
| 1.26 | F | F | H | COOC$_2$H$_5$ | 3-Cl | 5-CF$_3$ | |
| 1.27 | F | F | H | COO—C$_6$H$_5$ | H | H | |
| 1.28 | Br | Br | H | C(O)—C(O)—OCH$_3$ | H | H | |
| 1.29 | Cl | Cl | H | C(O)—C(O)—OC$_2$H$_5$ | 3-Cl | 5-CF$_3$ | |
| 1.30 | Cl | Cl | H | COSCH$_3$ | H | H | |
| 1.31 | Cl | Cl | CH$_3$ | COOCH$_3$ | H | H | |
| 1.32 | Cl | Cl | H | [2,6-dichloropyridin-4-yl-CO] | H | H | 204–208° C. |
| 1.33 | Cl | Cl | CH$_3$ | C(O)—C(O)—OCH$_3$ | H | H | |
| 1.34 | Cl | Cl | H | COCH$_3$ | 3-Cl | 5-Cl | |
| 1.35 | Br | Br | H | COCH$_3$ | 3-Cl | 5-Cl | |
| 1.36 | F | F | H | COCH$_3$ | 3-Cl | 5-Cl | |
| 1.37 | Cl | Cl | H | COCH$_3$ | 5-CH$_3$ | H | |
| 1.38 | Br | Br | H | COC$_2$H$_5$ | 5-CH$_3$ | H | |
| 1.39 | Cl | Cl | CH$_3$ | COCH$_3$ | 3-Cl | 5-CH$_3$ | |
| 1.40 | Cl | Cl | H | COCH$_3$ | 3-Cl | 5-CH$_3$ | |
| 1.41 | Cl | Cl | H | COCH$_3$ | 3-CF$_3$ | 6-Cl | |
| 1.42 | Cl | Cl | H | COCH=CHCH$_3$ | H | H | m.p. 112–115° C. |
| 1.43 | Cl | Cl | CH$_3$ | COCH$_3$ | H | H | |
| 1.44 | Cl | Cl | CH$_3$ | COCH$_3$ | 3-Cl | 5-CF$_3$ | |
| 1.45 | Br | Br | CH$_3$ | [furan-2-yl-CO] | H | H | |
| 1.46 | I | I | CH$_3$ | COC$_2$H$_5$ | H | H | |
| 1.47 | Cl | Cl | H | COCH$_2$Cl | 3-Cl | 5-CF$_3$ | |
| 1.48 | Cl | Cl | H | COCCl$_3$ | H | H | |
| 1.49 | Cl | Cl | H | COCHCl$_2$ | H | H | |
| 1.50 | Cl | Cl | H | COCH$_2$SCH$_3$ | H | H | |
| 1.51 | Cl | Cl | H | CO(CH$_2$)$_2$SCH$_3$ | 3-Cl | 5-CF$_3$ | |
| 1.52 | Br | Br | H | [4-CF$_3$-phenyl-CO] | H | H | |

TABLE 1-continued

Compounds of formula

[Structure: Pyridine ring with X₂ (top), X₁ (bottom), and N, connected via CO—N(R₁)—N(R₂)— to another pyridine ring with R₃ and R₄ substituents]

| Compound | X₁ | X₂ | R₁ | R₂ | R₃ | R₄ | physical data |
|---|---|---|---|---|---|---|---|
| 1.53 | I | I | H | CO—C₆H₃(OCH₃) (para-OCH₃ phenyl) | 3-Cl | 5-CF₃ | |
| 1.54 | Cl | Cl | H | CO—C₆H₃(Cl)(Cl) (2,3-dichlorophenyl) | H | H | |
| 1.55 | Cl | Cl | H | CO—C₆H₄(Cl) (meta-Cl phenyl) | 6-Cl | H | |
| 1.56 | I | I | H | CO—C₆H₄(NO₂) (para-NO₂ phenyl) | H | H | |
| 1.57 | F | F | H | CO—C₆H₃(Cl) (meta-Cl phenyl) | H | H | |
| 1.58 | Cl | Cl | H | CO—(pyridyl, N ortho) | H | H | |
| 1.59 | Cl | Cl | H | CO—(pyridyl, N ortho) | 3-Cl | 5-CF₃ | |
| 1.60 | Cl | Cl | CH₃ | CO—(pyridyl, N para) | 3-Cl | H | |
| 1.61 | Cl | Cl | H | CO—(5-methyl-furan-2-yl) | H | H | |

TABLE 1-continued

Compounds of formula

| Compound | X₁ | X₂ | R₁ | R₂ | R₃ | R₄ | physical data |
|---|---|---|---|---|---|---|---|
| 1.62 | Cl | Cl | H | CO-(2,5-dimethylfuran-3-yl) | H | H | |
| 1.63 | Cl | Cl | H | CO-(cyclopropyl) | 3-Cl | 5-CF$_3$ | |
| 1.64 | Cl | Cl | H | CO-(2-chlorothiazol-5-yl) | H | H | |
| 1.65 | Cl | Cl | CH$_3$ | CO-(4-methyl-2-chlorothiazol-5-yl) | H | H | |
| 1.66 | Cl | Cl | H | CO-(4-trifluoromethyl-2-chlorothiazol-5-yl) | H | H | |
| 1.67 | Cl | Cl | H | CO-(4-methyl-1,3,4-thiadiazol-5-yl) | H | H | |
| 1.68 | Cl | Cl | H | CO-(2-methoxyphenyl) | H | H | |
| 1.69 | Cl | Cl | H | CO-(2-hydroxyphenyl) | H | H | |
| 1.70 | Cl | Cl | H | CO—CH$_2$CH(CH$_3$)$_2$ | H | H | m.p. 123–126° C. |
| 1.71 | Cl | Cl | H | CO—CH$_2$OCH$_3$ | 3-Cl | 5-CF$_3$ | m.p. 139–142° C. |
| 1.72 | Cl | Cl | H | CO(CH$_2$)$_2$CH$_3$ | H | H | m.p. 148–150° C. |
| 1.73 | Cl | Cl | * | CO(CH$_2$)$_5$CH$_3$ | H | H | m.p. 90–92° C. |
| 1.74 | Cl | Cl | ** | COCH$_3$ | H | H | m.p. 116–117° C. |

TABLE 1-continued

Compounds of formula

| Compound | X₁ | X₂ | R₁ | R₂ | R₃ | R₄ | physical data |
|---|---|---|---|---|---|---|---|
| 1.75 | Cl | Cl | H | COCH₃ | 5-NO₂ | H | |
| 1.76 | Cl | Cl | H | COC₂H₅ | 5-NO₂ | H | |
| 1.77 | Br | Br | H | COC₂H₅ | 5-NO₂ | H | |

*CO(CH₂)₅CH₃
**COCH₃

TABLE 2

Compounds of formula

| Compound | X₁ | X₂ | R₁ | R₃ | R₄ | physical data |
|---|---|---|---|---|---|---|
| 2.1 | Cl | Cl | H | H | H | m.p. 196–199° C. |
| 2.2 | Cl | Cl | H | 3-Cl | 5-CF₃ | m.p. 154–155° C. |
| 2.3 | Br | Br | H | H | H | m.p. 187–190° C. |
| 2.4 | Br | Br | H | 3-Cl | 5-CF₃ | |
| 2.5 | Cl | Cl | H | 3-Cl | 5-CH₃ | |
| 2.6 | Cl | Cl | H | 4-CCl₃ | 6-Cl | |
| 2.7 | Cl | Cl | H | 4-CCl₃ | 6-OCH₃ | |
| 2.8 | Cl | Cl | H | 4-COOCH₃ | 6-Cl | |
| 2.9 | I | I | H | H | H | |
| 2.10 | I | I | H | 3-Cl | 5-CF₃ | |
| 2.11 | F | F | H | H | H | |
| 2.12 | F | F | H | 3-Cl | 5-CF₃ | |
| 2.13 | Cl | Cl | H | 3-CF₃ | 6-Cl | |
| 2.14 | Cl | Cl | H | 5-CH₃ | H | |
| 2.15 | Br | Br | H | 5-CH₃ | H | |
| 2.16 | Cl | Cl | H | 3-Cl | 5-Cl | |
| 2.17 | Cl | Cl | CH₃ | H | H | |
| 2.18 | Cl | Cl | CH₃ | 3-Cl | 5-CF₃ | |
| 2.19 | Cl | Cl | CH₃ | 4-COOCH₃ | 6-Cl | |
| 2.20 | Cl | Cl | CH₃ | 5-CH₃ | H | |
| 2.21 | Br | Br | CH₃ | H | H | |
| 2.22 | Br | Br | CH₃ | 3-Cl | 5-CF₃ | |
| 2.23 | F | F | CH₃ | H | H | |
| 2.24 | I | I | CH₃ | H | H | |

In the above described preparatory processes the use of acyl halides which additionally contain active halogen atoms may cause cyclisation reactions to take place in the molecule of the final products, accompanied by salt formation. An example of this kind is:

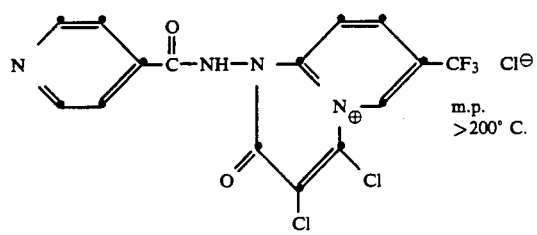

m.p. >200° C.

2. FORMULATION EXAMPLES FOR LIQUID ACTIVE INGREDIENTS OF FORMULA I (THROUGHOUT, PERCENTAGES ARE BY WEIGHT)

| 2.1. Emulsifiable concentrates | a) | b) | c) |
|---|---|---|---|
| a compound of Tables 1 and 2 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2. Solutions | a) | b) | c) | d) |
|---|---|---|---|---|
| a compound of Tables 1 and 2 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

| 2.3. Granulates | a) | b) |
|---|---|---|
| a compound of Tables 1 and 2 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | a) | b) |
|---|---|---|
| a compound of Tables 1 and 2 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient. Formulation Examples for solid active ingredients of formula I (throughout, percentages are by weight)

| 2.5. Wettable powders | a) | b) | c) |
|---|---|---|---|
| a compound of Tables 1 and 2 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of Tables 1 and 2 | 10% |
| octylphenol polyethlene glycol ether (4-5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required concentration can be obtained from this concentrate by dilution with water.

| 2.7. Dusts | a) | b) |
|---|---|---|
| a compound of Tables 1 and 2 | 5% | 8% |
| talcum | 95% | — |
| kaolin | — | 92% |

Ready-for-use dusts are obtained by mixing the active ingredient with the carrier, and grinding the mixture in a suitable mill.

| 2.8. Extruder granulate | |
|---|---|
| a compound of Tables 1 and 2 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Tables 1 and 2 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| a compound of Tables 1 and 2 | 40% |
| ethylene glycol | 10% |

| -continued | |
|---|---|
| 2.10. Suspension concentrate | |
| nonylphenol polyethylene glycol (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

EXAMPLE 3.1: Action against *Colletotrichum lagenarium* on *Cucumis sativus* L a) Residual-protective action After a cultivation period of 2 weeks, cucumber plants are sprayed with a spray mixture (concentration: 200 ppm) prepared from a wettable powder formulation of the test compound.

After 48 hours the plants are infected with a spore suspension ($1.5.10^5$ spores/ml) of the fungus and incubated for 36 hours at high humidity and a temperature of 23° C. Incubation is then continued at normal humidity and at 22°-23° C.

Evaluation of the protective action is made on the basis of fungus infestation 7-8 days after infection.

b) Systemic action

After a cultivation period of 2 weeks, cucumber plants are treated by soil application with a spray mixture prepared from a wettable powder formulation of the test compound (concentration: 60 or 220 ppm, based on the volume of the soil).

After 48 hours the plants are infected with a spore suspension ($1.5.10^5$ spores/ml) of the fungus and incubated for 36 hours at high humidity and a temperature of 23° C. Incubation is then continued at normal humidity and at 22° C.

Compounds of Tables 1 and 2 exhibited good activity in tests a) and b). Thus, for example, compounds 1.1, 1.4, 1.5, 1.6, 1.7, 1.10, 1.11, 1.13, 1.33, 1.72, 1.73, 1.74, 1.75, 2.1, 2.2 and 2.3 reduced fungus attack to 0 to 20%, whereas infestation with Colletotrichum was 100% on untreated, infected control plants.

EXAMPLE 3.2: Action against *Puccinia graminis* on wheat a) Residual-protective action Wheat plants are treated 6 days after sowing with a spray mixture (0.02% a.i.) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

b) Systemic action

Wheat plants are treated 5 days after sowing with a spray mixture (0.006% a.i., based on the volume of the soil) prepared from a wettable powder formulation of the test compound. After 48 hours the treated plants are infected with a uredospore suspension of the fungus.

The plants are then incubated for 48 hours at 95-100% relative humidity and about 20° C. and then stood in a greenhouse at about 22° C. Evaluation or rust pustule development is made 12 days after infection.

Compounds of Tables 1 and 2 exhibited good activity against Puccinia fungi. Thus, for example, in test (a), compounds 1.1, 1.5, 1.7, 1.16, 1.33, 1.43, 1.74, 1.75, 2.1, 2.2 and 2.3 and, in test (b), compounds 1.1, 1.3, 1.72 and 1.73, reduced fungus attack to 0 to 20%. On the other hand, Puccinia attack was 100% on untreated and infected control plants.

EXAMPLE 3.3: Action against *Phytophthora infestans* on tomato plants a) Residual-protective action After a cultivation period of 3 weeks, tomato plants are sprayed with a spray mixture (0.02% a.i.) prepared from a wettable powder formulation of the test compound. After 24 hours the tomato plants are infected with a sporangia suspension of the fungus. Evaluation of fungus attack is made after the plants have been incubated for 5 days at 90-100% relative humidity and 20° C.

b) Systemic action

After a cultivation period of 3 weeks, tomato plants are sprayed with a spray mixture (0.006% a.i., based on the volume of the soil) prepared from a wettable powder formulation of the test compound. Care is taken that the spray mixture does not come into contact with the growing parts of the plants. After 48 hours the treated plants are infected with a sporangia suspension of the fungus. Evaluation of fungus attack is made after the infected plants have been incubated for 5 days at 90-100% relative humidity and 20° C.

Compounds of Tables 1 and 2 exhibited good systemic action against the Phytophthora fungus. Thus, for example, in test (a), compounds 1.1, 1.72 and 1.73 and, in test (b), compounds 1.1, 1.33, 1.71 and 2.2, reduced fungus attack to 0 to 20%, whereas Phytophthora attack was 100% on untreated and infected control plants.

EXAMPLE 3.4: Action against *Cercospora arachidicola* on groundnut plants Residual protective action Groundnut plants 10-15 cm in height are sprayed with a spray mixture (0.006% a.i.) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected control plants (number and size of the specks=100%), Cercospora attack on groundnut plants treated with compounds of Tables 1 and 2 was substantially reduced.

EXAMPLE 3.5: Action against *Plasmopara viticola* on vines a) Residual protective action Vine seedlings in the 4-5 leaf stage are sprayed with a spray mixture (0.02% a.i.) prepared from a wettable powder formulation of the test compound. After 24 hours the treated plants are infected with a sporangia suspension of the fungus. Fungus attack is evaluated after incubation for 6 days at 95-100% relative humidity and 20° C.

b) Residual-curative action

Vine seedlings in the 4-5 leaf stage are infected with a sporangia suspension of the fungus. After incubation for 24 hours in a humid chamber at 95-100% relative humidity and 20° C., the infected plants are dried and sprayed with a spray mixture (0.06% a.i.) prepared from a wettable powder formulation of the test compound. After the spray coating has dried, the treated plants are once more placed in the humid chamber. Evaluation of fungus infestation is made 6 days after infection.

Compounds of Tables 1 and 2 exhibited good fungicidal activity against Plasmopara viticola, whereas Plasmopara attack was 100% on untreated and infected control plants.

EXAMPLE 3.6: Action against *Pyricularia oryzae* on rice plants a) Residual protective action After a cultivation period of 2 weeks, rice plants are sprayed with a spray mixture (0.02% a.i.) prepared from a wettable powder formulation of the test compound. After 48 hours the treated plants are infected with a conidia suspension of the fungus. Evaluation of fungus attack is made after incubation for 5 days at 95-100% relative humidity and 24° C.

b) Systemic action

A spray mixture (0.006% a.i., based on the volume of the soil) prepared from a wettable powder formulation of the test compound is poured onto two-week-old rice plants growing in earthenware pots customarily used for flowers. The pots are then filled with water until the lowermost stem parts of the rice plants are standing in water. After 96 hours the treated rice plants are infected with a conidia suspension of the fungus. Evaluation of fungus attack is made after incubation of the infected plants for 5 days at 95 to 100% relative humidity and about 24° C.

In comparison with untreated control plants (100% attack), fungus infestation was only slight on rice plants which were treated with a spray mixture containing, as active component, a compound of Tables 1 and 2. Thus, for example, in test (a), compounds 1.7, 1.71, 1.72, 1.73 and 2.3 and, in test (b), compounds 1.12, 1.16, 1.43, 1.71, 1.72, 1.73, 1.74 and 2.3, reduced fungus attack to 5-20%.

EXAMPLE 3.7: Immunising action against *Colletotrichum lagenarium* on *Cucumis sativus* L.

After a 2 week cultivation period, cucumber plants are sprayed with a spray mixture (concentration: 200 ppm) prepared from a wettable powder formulation of the test compound. After 3 weeks the plants are infected with a spore suspension ($1.5.10^5$ spores/ml) of the fungus and incubated for 36 hours at high humidity and at 23° C. Incubation is then continued at normal humidity and at 22°-23° C.

Evaluation of the protective action is made on the basis of the fungus infestation 7-8 days after infection.

Fungus attack was 100% on untreated and infected control plants.

Compounds of Tables 1 and 2 effected good immunisation against Colletotrichum.

EXAMPLE 3.8: Immunising action against tobacco mosaic virus on tobacco 8-week-old tobacco plants are sprayed (concentration: 200 ppm) or injected (concentration: 200 ppm) with a formulated solution of the test compounds. After 4 days the plants are mechanically inoculated with a suspension of tobacco mosaic virus (0.5 μg/ml + carborundum) and incubated at a temperature of 20°-22° C.

Evaluation of the protective action is made on the basis of the number and size of the local lesions 7 days after inoculation.

Compounds of Tables 1 and 2 effected good immunisation against tobacco mosaic virus, with e.g. compounds 1.1 and 1.3 being outstanding. On the other hand, lesions were 100% on infected and untreated control plants.

EXAMPLE 3.9: Action against *Pseudomonas lachrymans* on *Cucumis sativus* L a) Residual-protective action After a 2 week cultivation period, cucumber plants are sprayed with a spray mixture (concentration: 200 ppm) prepared from a wettable powder formulation of the test compound.

After 1 week the plants are infected with a bacterial suspension ($10^8$ bacteria/ml) and incubated for 7 days at high humidity and at 23° C. Evaluation of the protective action is made on the basis of bacterial attack 7-8 days after infection.

b) Systemic action

After a 2 week cultivation period, cucumber plants are treated by soil application with a spray mixture (concentration: 60, 20, 6, and 2 ppm, based on the volume of the soil) prepared from a wettable powder formulation of the test compound.

After 1 week the plants are infected with a bacterial suspension ($10^8$ bacteria/ml) and incubated for 7 days at high humidity and 23° C.

Evaluation of the protective action is made on the basis of bacterial attack 7-8 days after infection.

Compounds of Tables 1 and 2 exhibited good protective action against infestation by Pseudomonas. Thus, for example, in tests (a) and (b) compound 1.1 reduced bacterial attack to 0-10%, whereas Pseudomonas attack was 100% on untreated and infected control plants.

EXAMPLE 3.10: Action against *Xanthomonas oryzae* on rice (*Oryza sativa*)

a) Residual-protective action

Three weeks after being cultivated in a greenhouse, rice plants of the variety "Caloro" or "S6" are sprayed with a spray mixture (0.02% a.i.) prepared from a wettable powder formulation of the test compound. The spray coating is left to dry for 1 day and the plants are then put into a controlled environment chamber at 24° and 75-85% relative humidity and infected by cutting off the tips of the leaves with scissors which have been dipped beforehand in a suspension of *Xanthomonas oryzae*. After incubation for 10 days in the same room, the cut leaves wither, roll up and become necrotic. The residual effectiveness of the test compound is assessed by determining the extent of these symptoms.

b) Systemic action

Three weeks after being reared in a greenhouse, rice plants of the variety "Caloro" or "S6" are treated with a suspension prepared from a 25% wettable powder formulation of the test compound (0.006% a.i., based on the volume of the soil). Three days after this treatment the plants are put into a controlled environment chamber at 24° C. and 75-85% relative humidity and infected by cutting off the tips of the leaves with scissors which have been dipped beforehand in a suspension of *Xanthomonas oryzae*. After incubation for 10 days in the same room, the cut leaves wither, roll up and become necrotic. The systemic action of the test compound is assessed by determining the extent of these symptoms.

Compounds of Tables 1 and 2 exhibited good action against *Xanthomonas oryzae*. Thus, for example, in test (a), compounds 1.6, 1.33, 2.1 and 2.2 and, in test (b), compounds 1.1, 1.3, 1.4, 1.8, 1.10, 1.11, 1.33, 1.71, 1.73, 2.1, 2.2 and 2.3 reduced fungus infestation to 0-20%. On the other hand, Xanthomonas infestation was 100% on untreated, infected control plants.

EXAMPLE 3.11: Action against *Xanthomonas vesicatoria* on paprika plants (*capsicum annum*)

a) After a 3 week cultivation period in a greenhouse, paprika plants of the California wonder variety are sprayed with the test compound formulated as spray mixture (0.02% a.i.). After the spray coating has been left to dry for 1 day the plants are placed in a controlled environment chamber at 26° C. and 95-100% relative humidity and infected by spraying the underside of the leaves with a standardised suspension of *Xanthomonas vesicatoria*. After incubation for 6 days, round, initially watery and later necrotic, whitened specks form on the leaves. The residual effectiveness of the test compound is assessed by determining the extent of these specks.

b) Systemic action

After a 3 week cultivation period in a greenhouse, paprika plants of the California wonder variety are treated with a suspension of the test compound (0.006% a.i., based on the volume of the soil). Three days after this treatment the plants are placed in a controlled environment chamber at 26° C. and 95-100% relative humidity and infected by spraying the underside of the leaves with a standardised suspension of *Xanthomonas vesicatoria*. After incubation for 6 days, round, initially watery and later necrotic, whitened specks form on the leaves. The residual effectiveness of the test compound is assessed by determining the extent of these specks.

Compounds of Tables 1 and 2 exhibited good activity against *Xanthomonas vesicatoria*. Thus, for example, in test (a), compounds 1.1, 1.3, 1.33, 2.1 and 2.2 and, in test (b) compounds 1.1, 1.3, 1.4, 1.8, 1.10, 1.11, 1.33, 1.71, 1.73, 2.1 and 2.2 reduced bacterial attack to 0-20%. On the other hand, infestation was 100% on untreated and infected control plants.

EXAMPLE 3.12: Action against *Fusarium nivale* on rye

Rye seeds of the Tetrahell variety which are naturally infected with *Fusarium nivale* are dressed on a mixer roll with the test fungicide at concentrations of 600, 200 or 60 ppm a.i. (based on the weight of the seeds). The infected and treated rye is sown in October in the open with a seeder in plots 3 meters long and in 6 rows. Three replicates are carried out with each test compound. Until evaluation is made, the test plants are cultivated under normal field conditions (preferably in a region with unbroken snow cover during the winter months). To determine the effectiveness of the test compounds, the percentage of plants infested with Fusarium is assessed in the spring directly after the snow has melted.

Compounds of Tables 1 and 2 exhibited good activity against Fusarium on rye in this test. On the other hand, infestation was 100% on untreated and infected control plants.

EXAMPLE 3.13: Action against *Helminthosporium gramineum* on barley

Seeds of winter barley of the "Cl" variety which are naturally infected with *Helminthosporium gramineum* are dressed on a mixer roll with the test compound at a concentration of 600, 200 or 60 ppm a.i. (based on the weight of the seeds). The infected and treated barley is sown in October in the open with a seeder in plots 2 meters long and in 3 rows. Three replicates are carried out with each test compound. Until evaluation is made, the test plants are cultivated under normal field conditions. To determine the effectiveness of the test compounds, the percentage of stalks attacked by Helminthosporium is assessed at the time of ear emergence.

Compounds of Tables 1 and 2 exhibited good activity against Helminthosporium in this test. On the other hand, infestation was 100% on untreated and infected control plants.

EXAMPLE 3.14: Action against *Ustilago nuda* on barley (seed dressing)

Seeds of winter barley of the "RM1" variety which are naturally infected with *Ustilago nuda* are dressed on a mixer roll with the test compound at a concentration of 600, 200 or 60 ppm a.i. (based on the weight of the seeds). The infected and treated barley is sown in October in the open with a seeder in plots 2 meters long and in 3 rows. Three replicates are carried out with each test compound at its given concentration. Until evaluation is made, the test plants are cultivated under normal field conditions. To determine the effectiveness of the test compounds, the percentage of ears attacked by Ustilago is assessed during flowering.

EXAMPLE 3.15: Action against *Colletotrichum lagenarium* on *Cucumis sativa* (seed dressing)

Cucumber seeds are dressed with a solution of the test compound (concentration: 180 g/100 kg of seeds). The seeds are then sown and, after 4 weeks, the plants are infected with a spore suspension $1.5.10^5$ spores/ml) of the fungus and incubated for 36 hours at high humidity and a temperature of 23° C. Incubation is then continued at normal humidity and 22°-23° C. Evaluation of the protective action is made on the basis of fungus infestation 7-8 days after infection.

Compounds of Tables 1 and 2 exhibited good activity against Colletotrichum. Thus, for example, compounds 1.1 and 2.2 reduced infestation to 0–20%, whereas fungus infestation was 100% on control plants whose seeds were not treated.

EXAMPLE 3.16: Residual protective action against *Venturia inaequalis* on apple shoots Apple cuttings with 10-20 cm long fresh shoots are sprayed with a spray mixture (0.02% a.i.) prepared from a wettable powder formulation of the test compound. The plants are infected 24 hours later with a conidia suspension of the fungus. The plants are then incubated for 5 days at 90-100% relative humidity and stood in a greenhouse for a further 10 days at 20°-24° C. Scab infestation is evaluated 15 days after infection.

Compounds of Tables 1 and 2 exhibited good activity against Venturia. Thus, for example, compounds 1.71 and 2.2 reduced scab infestation to 5–20%, whereas Venturia infestation was 100% on untreated and infected shoots.

EXAMPLE 3.17: Action against *Cercospora nicotianae* on tobacco plants 8-week-old tobacco plants are injected with a formulated solution of the test compound (concentration: 200 ppm). Over a period of 2 hours to 4 days after treatment, the plants are sprayed with a spore suspension of *Cercospora nicotianae* ($10^5$ spores/ml) and then incubated for 5 days at high humidity and a temperature of 22°-25° C. Incubation is then continued at normal humidity and 20°-22° C. Evaluation of the symptoms is then made on the basis of the fungus infestation 12-14 days after infection.

Compounds of Tables 1 and 2 exhibited good activity against Cercospora. Thus, for example, compound 1.1 reduced fungus infestation to 0–20%, whereas infestation was 100% on infected control plants.

What is claimed is:

1. A compound of formula I

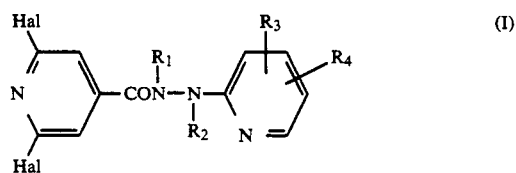

wherein
Hal is halogen,
$R_1$ is selected from the group consisting of hydrogen, methyl and $-COR_5$,
$R_2$ is

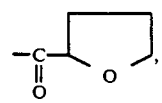

$R_3$ is hydrogen, halogen, trifluoromethyl, trichloromethyl, $-COOH$, $-COOCH_3$, $-OH$ or nitro,
$R_4$ is hydrogen, halogen, trifluoromethyl, methoxy or methyl,
$R_5$ is $C_1-C_6$alkyl, unsubstituted or substituted by one or more halogen atoms, $C_1-C_6$alkyl which is interrupted by oxygen or sulfur, $C_1-C_6$alkyl which is substituted by one or more halogen atoms and interrupted by oxygen or sulfur; $C_2-C_4$alkenyl, unsubstituted or substituted by one or more halogen atoms; phenyl, benzyl, or phenyl or benzyl each substituted by halogen, methyl, trifluoromethyl or trichloromethyl; or a 3- to 6-membered cycloalkyl radical or a cycloalkyl radical which is substituted by one or more halogen atoms or methyl groups.

2. A compound of formula I according to claim 1, wherein
Hal is chlorine or bromine;
$R_1$ is hydrogen; and
$R_3$ and $R_4$ are each independently of the other hydrogen, halogen or trifluoromethyl.

3. A compound of formula I according to claim 1, wherein
Hal is chlorine;
$R_1$ is hydrogen; and
$R_3$ and $R_4$ are each independently of the other hydrogen, halogen or trifluoromethyl.

4. A compound of formula I according to claim 1, wherein
Hal is chlorine;
$R_1$ is hydrogen;
$R_3$ is hydrogen or 3-chloro; and
$R_4$ is hydrogen or 5-trifluoromethyl.

5. The compound 1-(tetrahydrofuroyl-2)-1-(pyridinyl-2)-2-(2,6-dichloroisonicotinoyl)-hydrazine according to claim 1.

6. A composition for protecting plants against attack by microorganisms which contains as active component at least one compound of formula (I)

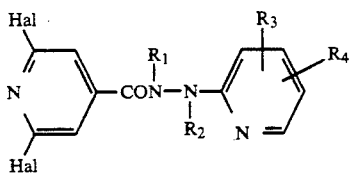

wherein
Hal is halogen,
$R_1$ is selected from the group consisting of hydrogen, methyl and —$COR_5$,
$R_2$ is

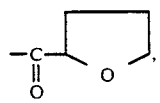

$R_3$ is hydrogen, halogen, trifluoromethyl, trichloromethyl, —COOH, —COOCH$_3$, —OH or nitro,
$R_4$ is hydrogen, halogen, trifluoromethyl, methoxy or methyl,
$R_5$ is $C_1$-$C_6$alkyl, unsubstituted substituted by one or more halogen atoms, $C_1$-$C_6$alkyl which is interrupted by oxygen or sulfur, $C_1$-$C_6$alkyl which is substituted by one or more halogen atoms and interrupted by oxygen or sulfur; $C_2$-$C_4$alkenyl, unsubstituted or substituted by one or more halogen atoms; phenyl, benzyl, or phenyl or benzyl each substituted by halogen, methyl, trifluoromethyl or trichloromethyl; or a 3- to 6-membered cycloalkyl radical or a cycloalkyl radical which is substituted by one or more halogen atoms or methyl groups.

7. A composition of claim 6 wherein
Hal is chlorine or bromine,
$R_1$ is hydrogen, and
$R_3$ and $R_4$ are each independently of the other hydrogen, halogen or trifluoromethyl.

8. A composition of claim 6 which contains 1-(tetrahydrofuroyl-2)-1-(pyridinyl-2)-2-(2,6-dichloroisonicotinoyl)-hydrazine as the active component.

9. A method of protecting plants from attack by photopathogenic microorganisms which comprises applying, to said plants or the locus thereof, an effective amount of a compound of formula (I)

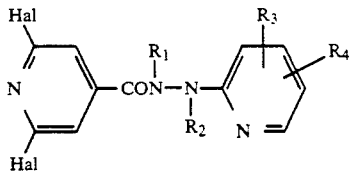

wherein
Hal is halogen,
$R_1$ is selected from the group consisting of hydrogen, methyl and —$COR_5$,
$R_2$ is

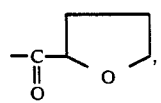

$R_3$ is hydrogen, halogen, trifluoromethyl, trichloromethyl, —COOH, —COOCH$_3$, —OH or nitro,
$R_4$ is hydrogen, halogen, trifluoromethyl, methoxy or methyl,
$R_5$ is $C_1$-$C_6$alkyl, unsubstituted or substituted by one or more halogen atoms, $C_1$-$C_6$alkyl which is interrupted by oxygen or sulfur, $C_1$-$C_6$alkyl which is substituted by one or more halogen atoms and interrupted by oxygen or sulfur; $C_2$-$C_4$alkenyl, unsubstituted or substituted by one or more halogen atoms; phenyl, benzyl, or phenyl or benzyl each substituted by halogen, methyl, trifluoromethyl or trichloromethyl; or a 3- to 6-membered cycloalkyl radical or a cycloalkyl radical which is substituted by one or more halogen atoms or methyl groups.

10. A method of claim 9 wherein Hal is chlorine or bromine;
$R_1$ is hydrogen; and
$R_3$ and $R_4$ are each independently of the other hydrogen, halogen or trifluoromethyl.

11. A method of claim 9 wherein the plants are immunized against attack by phytopathogenic microorganisms.

12. A method of claim 10 wherein the plants are immunized against attack by phytopathogenic microorganisms.

13. A method according to claim 9 wherein the phytopathogenic microorganisms are fungi.

14. A method according to claim 13, wherein the fungi are organisms of the classes Ascomycetes, Basidiomycetes or fungi imperfecti.

15. A method according to claim 9, wherein the phytopathogenic microorganisms are bacteria.

16. A method according to claim 9, wherein the phytopathogenic microorganisms are viruses.

17. A method of claim 9 wherein the compound of formula (I) is applied at a rate from 50 grams to 5 kilograms per hectare.

18. A method of claim 17 wherein the compound of formula (I) is applied at a rate from 100 grams to 2 kilograms per hectare.

19. A method of claim 18 wherein the compound of formula (I) is applied at a rate from 200 grams to 600 grams per hectare.

* * * * *